(12) United States Patent
Ono et al.

(10) Patent No.: US 7,259,849 B2
(45) Date of Patent: Aug. 21, 2007

(54) OPTICAL SYSTEM FOR MICRO ANALYZING SYSTEM

(75) Inventors: Koichi Ono, Saitama (JP); Teruo Fujii, Tokyo (JP); Serge Camou, Tokyo (JP)

(73) Assignee: Enplas Corporation, Saitama (JP)

( * ) Notice: Subject to any disclaimer, the term of this patent is extended or adjusted under 35 U.S.C. 154(b) by 399 days.

(21) Appl. No.: 10/859,485

(22) Filed: Jun. 2, 2004

(65) Prior Publication Data
US 2004/0246597 A1    Dec. 9, 2004

(30) Foreign Application Priority Data
Jun. 4, 2003    (JP)    ............... P2003-159772

(51) Int. Cl.
*G01N 21/00* (2006.01)
(52) U.S. Cl. ..................................... 356/344
(58) Field of Classification Search ........ 356/344–362; 359/362
See application file for complete search history.

(56) References Cited

U.S. PATENT DOCUMENTS

| 1,468,762 | A | * | 9/1923 | Taylor et al. | ............... | 359/362 |
| 4,680,977 | A | * | 7/1987 | Conero et al. | ........... | 73/861.41 |
| 5,213,673 | A | * | 5/1993 | Fujimiya et al. | ............ | 204/612 |
| 5,268,978 | A | * | 12/1993 | Po et al. | ........................ | 385/33 |
| 5,892,630 | A | * | 4/1999 | Broome | ...................... | 359/834 |
| 6,233,048 | B1 | * | 5/2001 | Parce | ......................... | 356/344 |
| 6,337,740 | B1 | * | 1/2002 | Parce | ......................... | 356/344 |
| 6,511,421 | B2 | * | 1/2003 | Forster | ....................... | 600/176 |
| 6,590,717 | B2 | * | 7/2003 | Sasano et al. | ............... | 359/717 |
| 6,690,467 | B1 | * | 2/2004 | Reel | ........................... | 356/328 |
| 6,839,188 | B2 | * | 1/2005 | Miura et al. | ................. | 359/718 |

FOREIGN PATENT DOCUMENTS

| JP | 11-64278 | 3/1999 |
| JP | 2002-214194 | 7/2002 |

OTHER PUBLICATIONS

2001 IEEE/LEOS, International Conference on Optical MEMS 2001. Sep. 25-28, 2001, pp. 133-134, S. Camou et al., Design of 2-D optical lens on a PDMS micro-chip to imp.

* cited by examiner

*Primary Examiner*—Gregory J. Toatley, Jr.
*Assistant Examiner*—Jarreas Underwood
(74) *Attorney, Agent, or Firm*—Bachman & LaPointe, P.C.

(57) ABSTRACT

There is provided an optical system 8 for a micro analyzing system capable of precisely analyzing a sample. In the optical system 8, after light beams leaving the tip of an optical fiber 14 pass through a condensing part 13, a sample moving in a separation passage 6 due to electrophoresis is irradiated with the light beams. The condensing part 13 includes a first aspherically cylindrical surface 10 being convex toward the optical fiber 14, a second aspherically cylindrical surface 11 being convex on the opposite side to the first aspherically cylindrical surface 10, and a third aspherically cylindrical surface 12 being convex toward the second aspherically cylindrical surface 11. The first through third aspherically cylindrical surfaces 10 through 12 are arranged in that order from the side of the optical fiber 14 toward the separation passage 6. The sample moving due to electrophoresis is irradiated with light beams which are condensed by the first through third aspherically cylindrical surfaces 10 through 11 after leaving the optical fiber 14.

10 Claims, 10 Drawing Sheets

FIG.5

| | Plane Number | Curvature c | Interval d | Refractive Index | Conical Constant k | Quaternary Aspheric Coefficient A |
|---|---|---|---|---|---|---|
| Outgoing Plane of Optical Fiber | | | 0.8411 | | | |
| Aspherically Cylindrical Surface 10 | S1 | 3.5903 | 0.2596 | 1.41 | -1.4657 | -0.5116 |
| Aspherically Cylindrical Surface 11 | S2 | -3.1786 | 0.5015 | 1.41 | -2.6967 | -0.2671 |
| Aspherically Cylindrical Surface 12 | S3 | 11.2474 | 0.1500 | | -3.0415 | 476.0815 |
| Condensing Surface | | | | | | |

NA(sin θ) = 0.25
Design Wavelength = 587.56 nm

OPTICAL SYSTEM FOR MICRO ANALYZING SYSTEM

BACKGROUND OF THE INVENTION

1. Field of the Invention

The present invention generally relates to an optical system for a micro analyzing system. More specifically, the invention relates to an optical system for a micro analyzing system used for optically analyzing a very small amount of sample in the field of chemistry, such as biochemistry or analytical chemistry, medicine or the like.

2. Description of the Prior Art

In recent years, there has been developed a micro analyzing system wherein a micro space, which functions as a flow passage, a reacting portion, a separating portion or a detecting portion, is formed in a microchip of a glass or plastic to rapidly process a very small amount of sample in the microchip. FIG. 9 shows an example of a microchip 41 for electrophoresis, to which a conventional optical system 48 for a micro analyzing system is applied. As shown in FIG. 9, the microchip 41 has a plate member 42 in which a sample passage 45 and a separation passage 46 are formed so as to cross each other. In the sample passage 45 and separation passage 46, a sample separating medium is previously filled. The microchip 41 is designed to separate and identify a sample by the following process. First, a sample is injected from one end portion of the sample passage 45, and a voltage is applied to both ends of the sample passage 45 to move the sample due to electrophoresis until the front end of the sample passes through a passage crossing portion 47. Then, a voltage is applied to both ends of the separation passage 46 to feed a very small amount of sample, which is positioned at the passage crossing portion 47, into the separation passage 46 to start the separation of the sample. As shown in FIGS. 10 and 11, the sample moving in the separation passage 46 due to electrophoresis has different electrophoretic speeds in accordance with a difference in molecular weight or the like, and is separated into a plurality of bands (a group of materials) 43 until it reaches the optical system 48. The sample (band 43) reaching the optical system 48 is irradiated with light beams from an optical fiber 54, and fluorescence emitted from the fluorescent label of the sample is detected by a detecting means (e.g., a light receiving element) 55 to analyze the sample (see, e.g., Japanese Patent Laid-Open Nos. 11-64278 and 2002-214194).

In such a conventional optical system 48 for the micro analyzing system which is applied to the microchip 41, light beams emitted from the tip of the optical fiber 54 connected to a light source (not shown) are condensed by a cylindrical lens 49 having a spherical lens surface viewed in directions perpendicular to the plane of FIGS. 10 and 11, and the sample (band 43) moving in the separation passage 46 due to electrophoresis is irradiated with the light beams condensed by the spherically cylindrical lens 49, so that fluorescence emitted from the sample is detected by the detecting means 55 (see S. Camou et al., "Design of 2-D optical lens on a PDMS micro-chip to improve fluorescence spectroscopy using integrated optical fibers", Optical MEMS 2001, 25-28, September 2001, pp. 133-134).

However, in the optical system 48 for the micro analyzing system shown in FIG. 10, the width (the width in directions in which the sample moves due to electrophoresis) of light beams obtained by condensing divergent beams, which are emitted from the optical fiber having a predetermined core diameter, by means of the spherically cylindrical lens 49 is large. Therefore, if the distance between adjacent two of the bands 43 is decreased as shown in FIG. 11, there are some cases where adjacent two or more of the bands 43 in the moving direction due to electrophoresis may be simultaneously irradiated with light beams, so that fluorescence simultaneously emitted from the plurality of bands 43 may be detected by the detecting means 55. In addition, there are some cases where fluorescence from a sample other than a target sample may be simultaneously picked up, so that the precise of analysis is not always satisfied. Moreover, in order to ensure the precision of analysis, if the distance between adjacent two of bands is increased so that only a target sample (band) is irradiated with measuring beams, the time required to carry out measurement increases. Thus, it is desired for research workers in the field of chemistry, such as biochemistry or analytical chemistry, medicine or the like to obtain an optical system for a micro analyzing system capable of more precisely and rapidly analyzing a sample.

SUMMARY OF THE INVENTION

It is therefore an object of the present invention to eliminate the aforementioned problems and to provide an optical system for a micro analyzing system capable of precisely and rapidly analyzing a sample.

In order to accomplish the aforementioned and other objects, according to one aspect of the present invention, there is provided an optical system for an analyzing system for irradiating a sample with light beams to optically analyze the sample, the optical system comprising: a first lens surface for receiving light beams from a light source via a light guide passage, the first lens surface being an aspheric surface which is convex toward the light guide passage; a second lens surface for receiving the light beams passing through the first lens surface, the second lens surface being an aspheric surface which is concave toward the first lens surface; and a third lens surface for receiving the light beams passing through the second lens surface, the third lens surface being an aspheric surface which is convex toward the second lens surface, the first, second and third lens surfaces being associated with each other for condensing the light beams toward the sample.

In this optical system, each of the aspheric surfaces may be an aspherically cylindrical surface. The sample may lie in a space formed in a plate member. In this case, the first, second and third lens surfaces may be formed in the plate member. In addition, the space may be a channel for allowing the sample to move due to electrophoresis. The light guide passage may be an optical fiber.

According to another aspect of the present invention, there is provided an optical system for an analyzing system for irradiating a sample with light beams to optically analyze the sample, the optical system comprising: a plurality of lens surfaces associated with each other for condensing light beams toward the sample, at least one of the plurality of lens surfaces being an aspheric surface.

In this optical system, the aspheric surface may be an aspherically cylindrical surface. The sample may lie in a space formed in a plate member. In this case, the plurality of lens surfaces may be formed in the plate member. In addition, the space may be a channel for allowing the sample to move due to electrophoresis. The light guide passage may be an optical fiber.

According to a further aspect of the present invention, there is provided an optical system for an analyzing system for irradiating a sample, which is in a space formed in a plate member, with light beams to optically analyze the sample, the optical system comprising: a first lens surface, formed in the plate member, for receiving light beams from a light source via a light guide passage, the first lens surface being an aspheric surface which is convex toward the light guide passage; a second lens surface, formed in the plate member, for receiving the light beams passing through the first lens surface, the second lens surface being an aspheric surface which is concave toward the first lens surface; and a third lens surface, formed in the plate member, for receiving the light beams passing through the second lens surface, the third lens surface being an aspheric surface which is convex toward the second lens surface, the first, second and third lens surfaces being associated with each other for condensing the light beams toward the sample.

BRIEF DESCRIPTION OF THE DRAWINGS

The present invention will be understood more fully from the detailed description given herebelow and from the accompanying drawings of the preferred embodiments of the invention. However, the drawings are not intended to imply limitation of the invention to a specific embodiment, but are for explanation and understanding only.

In the drawings:

FIG. 5 is a table showing design numerical values of first through third aspherically cylindrical surfaces forming a condensing part in the first preferred embodiment;

DESCRIPTION OF THE PREFERRED EMBODIMENTS

Referring now to the accompanying drawings, the preferred embodiments of the present invention will be described below in detail.

First Preferred Embodiment

Figure 1:
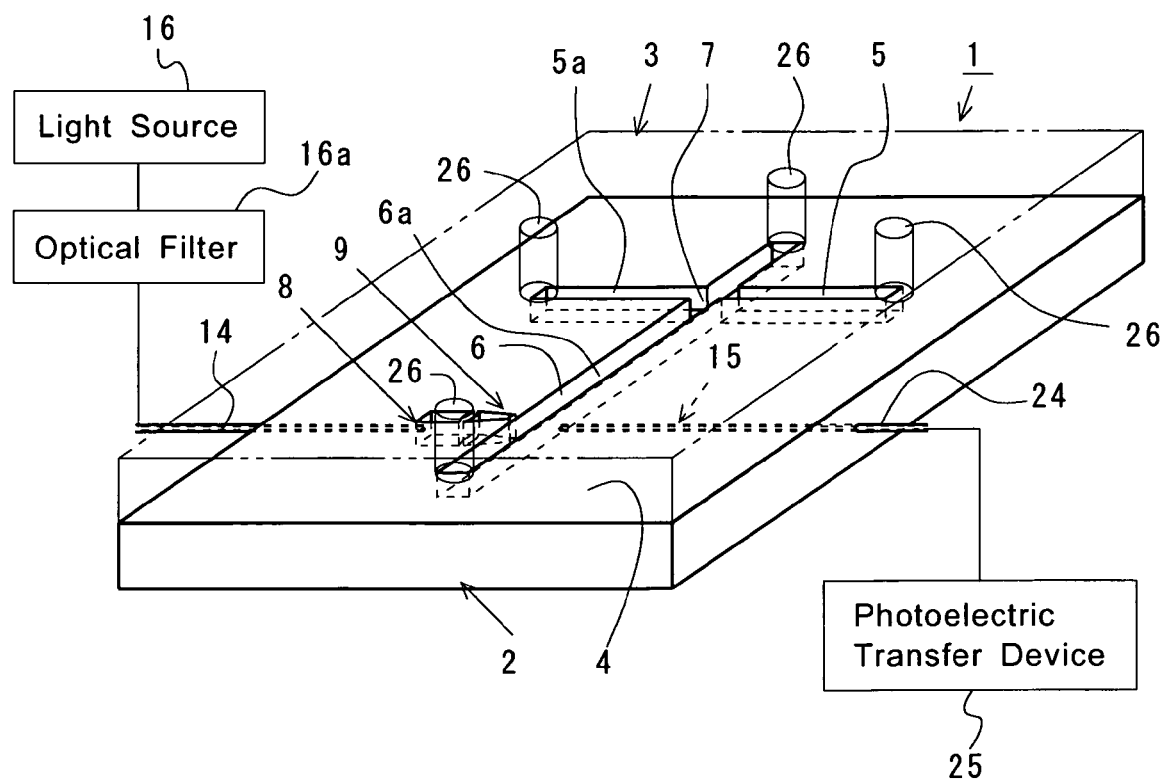
FIG. 1 is a perspective view of a microchip including the first preferred embodiment of an optical system for a micro analyzing system according to the present invention, wherein a second plate member is shown by a two-dot chain line for convenience of explanation.

FIG. 1 shows a microchip 1 for electrophoresis, to which the first preferred embodiment of an optical system for a micro analyzing system according to the present invention is applied. As shown in FIG. 1, the microchip 1 for electrophoresis comprises: a first plate member 2 of a resin or glass material having excellent optical characteristics, such as polydimethyl siloxane (PDMS), polycarbonate (PC), polymethyl methacrylate (PMMA), polystyrene (PS) or amorphous polyolefin; and a second plate member 3 (which is shown by a two-dot chain line for convenience of explanation) of the same material as that of the first plate member 2, the second plate member 3 being fixed to the first plate member 2 by adhesion, welding or the like. In a surface 4 (a surface to be bonded to the second plate member 3) of the first plate member 2, a first groove 5a having a substantially rectangular cross section, and a second groove 6a having a substantially rectangular cross section are formed so as to cross each other. By fixing the second plate member 3 to the surface 4 of the first plate member 2, the upper opening portions of the first groove 5a and second groove 6a are covered with the second plate member 4 to form a sample passage (first channel) 5 and a separation passage (second channel) 6, respectively. At a predetermined position of the separation passage 6 downstream of a passage crossing portion 7 in electrophoretic directions, there is arranged an analyzing part 9, which includes an optical system 8 for a micro analyzing system, for optically analyzing a sample moving in the separation passage 6 due to electrophoresis.

Figure 2:
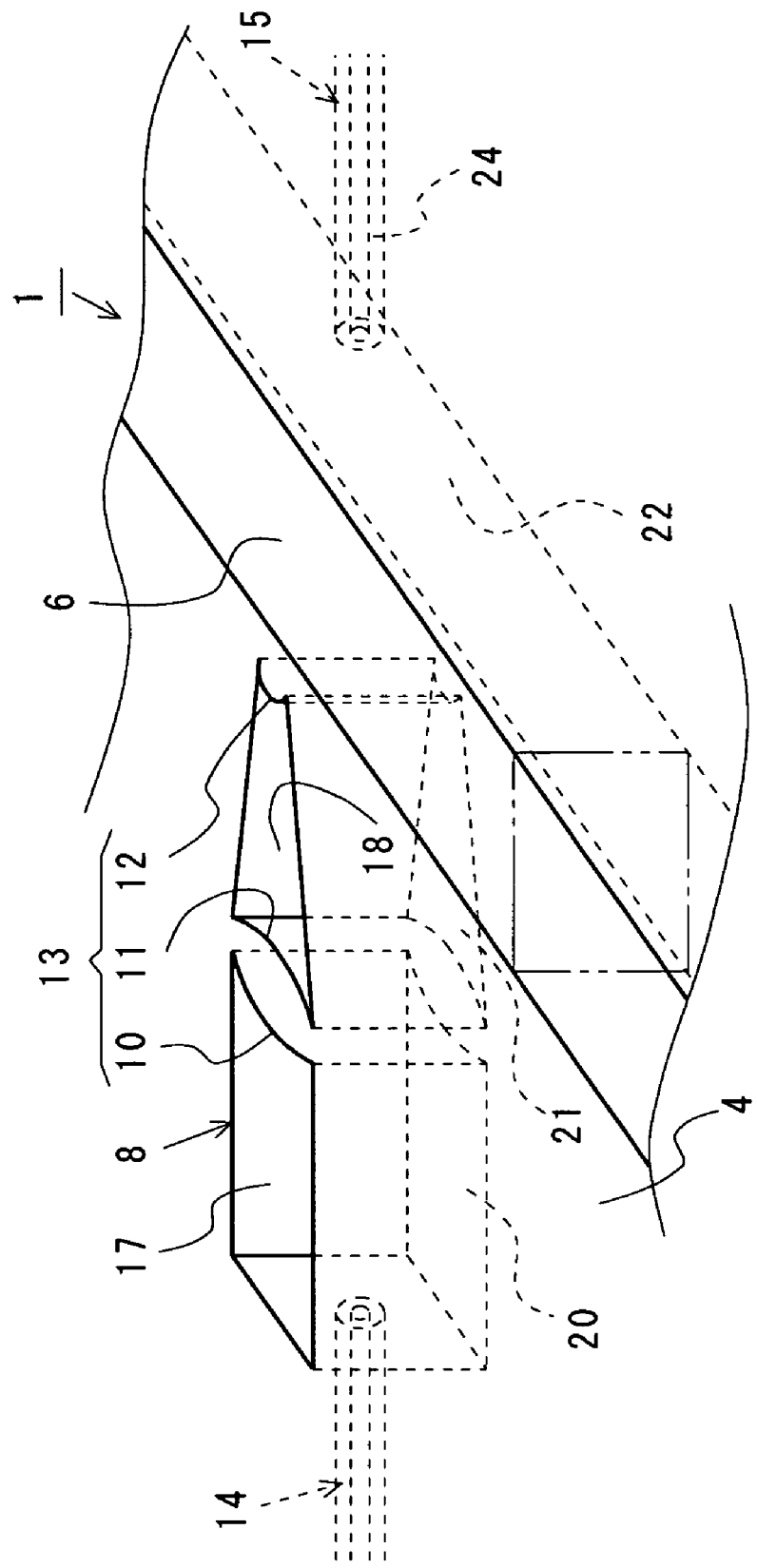
FIG. 2 is an enlarged perspective view of a part of a first plate member of the microchip including the optical system in the first preferred embodiment.
Figure 3:
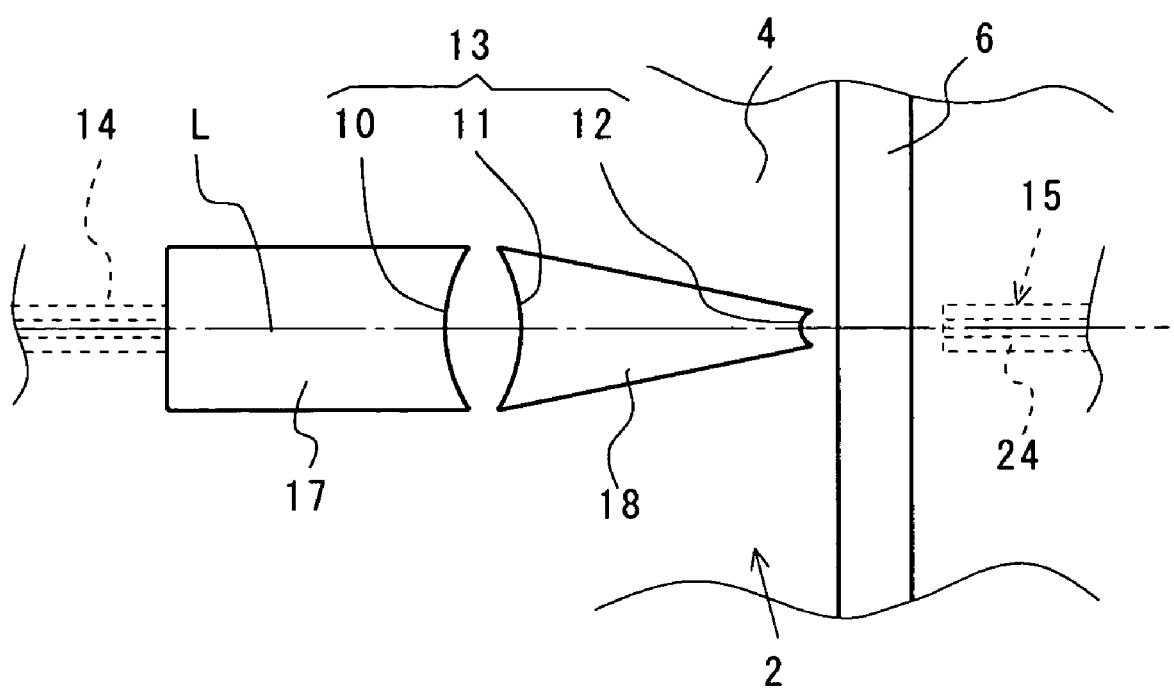
FIG. 3 is an enlarged plan view of a part of the first plate member of the microchip including the optical system in the first preferred embodiment.

As shown in FIGS. 2 and 3, the optical system 8 comprises a condensing part 13 and an optical fiber (light guide passage) 14, which are arranged on the side of one side of the separation passage 6. The condensing part 13 has three aspherically cylindrical surfaces 10, 11 and 12, which are aspheric lens surfaces viewed in directions perpendicular to the surface 4 of the first plate member 2 of the microchip 1 and which are vertical surfaces (curvature of 0) viewed in directions parallel to the surface 4 thereof. The optical fiber 14 has an outgoing plane for allowing light beams to travel toward the condensing part 13, and has a core diameter of 50 µm. The optical system 8 further comprises a detecting means 15 for detecting fluorescence emitted from a sample. The detecting means 15 is arranged on the side of the other side of the separation passage 6. The optical fiber 14 is connected to a light source 16 of a mercury lamp or the like via an optical filter means 16a. The optical fiber 14 is designed to receive light beams, which are emitted from the light source 16, from the plane of incidence to guide the light beams to the outgoing plane facing the condensing part 13, to allow divergent beams having a numerical aperture (NA) of 0.25 to leave the outgoing plane in the microchip 1 toward the condensing part 13. The light source 16 should not particularly be limited, but it may be a light emitting diode (LED) a laser, an electroluminescence (EL) or the like.

The condensing part 13 comprises a first aspherically cylindrical surface 10 arranged so as to face the tip of the optical fiber 14, a second aspherically cylindrical surface 11 arranged back to back with the first aspherically cylindrical surface 10, and a third aspherically cylindrical surface 12 arranged so as to face the second aspherically cylindrical surface 11. The first aspherically cylindrical surface 10 is formed so as to be convex toward the outgoing plane of the optical fiber 14. The second aspherically cylindrical surface 11 is formed so as to be convex in opposite directions to the first aspherically cylindrical surface 10 (concave toward the outgoing plane of the optical fiber 14). The second aspherically cylindrical surface 11 is formed so as to be integrated with the first aspherically cylindrical surface 10. The third aspherically cylindrical surface 12 is formed so as to be convex toward the second aspherically cylindrical surface 11 (convex toward the outgoing plane of the optical fiber 14). The first through third aspherically cylindrical surfaces 10 through 12 are sequentially arranged along an optical axis L from the optical fiber 14 toward the separation passage 6.

In the condensing part 13, a first space 17 between the tip of the optical fiber 15 and the first aspherically cylindrical surface 10 has a rectangular cross section perpendicular to the optical axis L, and has the same groove width from an end face, which is open to the tip of the optical fiber 14, to the first aspherically cylindrical surface 10. In addition, a second space 18 between the second aspherically cylindrical surface 11 and the third aspherically cylindrical surface 12 has a rectangular cross section perpendicular to the optical axis L, and has a width which gradually decreases toward the third aspherically cylindrical surface 12 as a distance from the second aspherically cylindrical surface 11 increases. The first and second spaces 17 and 18 are open to the surface (the top face in FIGS. 1 and 2) 4, and have bottom faces 20 and 21 which are substantially arranged on the same plane (at the same depth) as that of the bottom face 22 of the separation passage 6, respectively. Furthermore, the bottom faces 20 and 21 should not always be arranged on the same plane as that of the bottom face 22, and may be arranged so as to be lower (deeper) than the bottom face 22.

Figure 7:
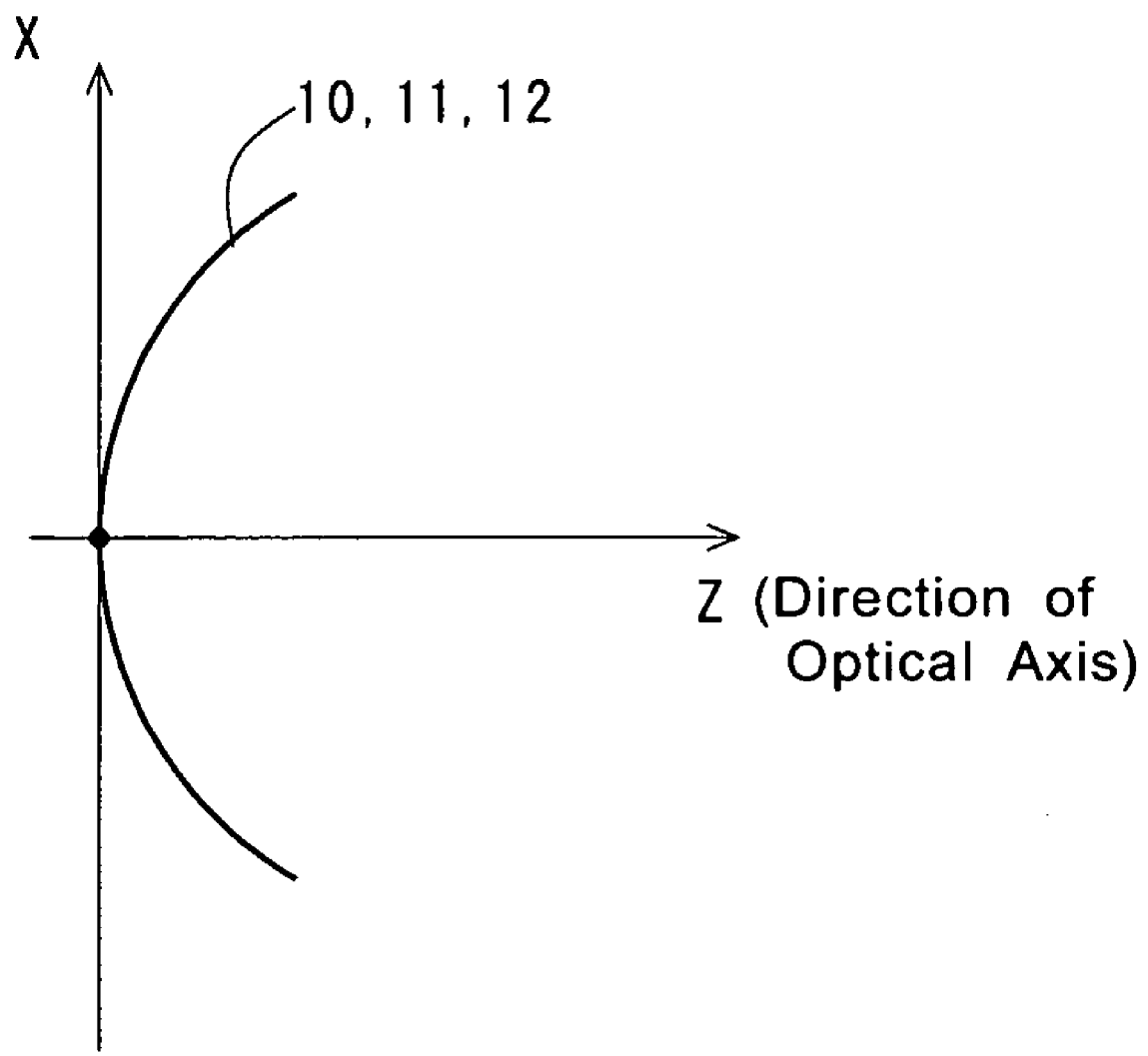
FIG. 7 is a diagram showing a cross section of an aspherically cylindrical surface.

As shown in FIG. 2, the first through third aspherically cylindrical surfaces 10 through 12 have the same shape in depth directions of the first or second space 17 or 18, respectively. The cross sections of each of the first through third aspherically cylindrical surfaces 10 through 12, which are taken along any lines in depth directions so as to be parallel to the bottom faces 20 and 21 of the first and second spaces 17 and 18, have the same shape as shown in FIG. 7, and are expressed by the following expression (1) and numerical values in FIG. 5, respectively:

$$Z = \frac{cX^2}{1 + \sqrt{1 - (k+1)c^2X^2}} + AX^4$$

wherein Z denotes a coordinate of a point on a plane in directions parallel to an optical axis, and X denotes a coordinate of the point on the plane from the optical axis, k denoting a conical constant, c denoting a curvature, and A denoting a quaternary aspheric coefficient.

Figure 4:
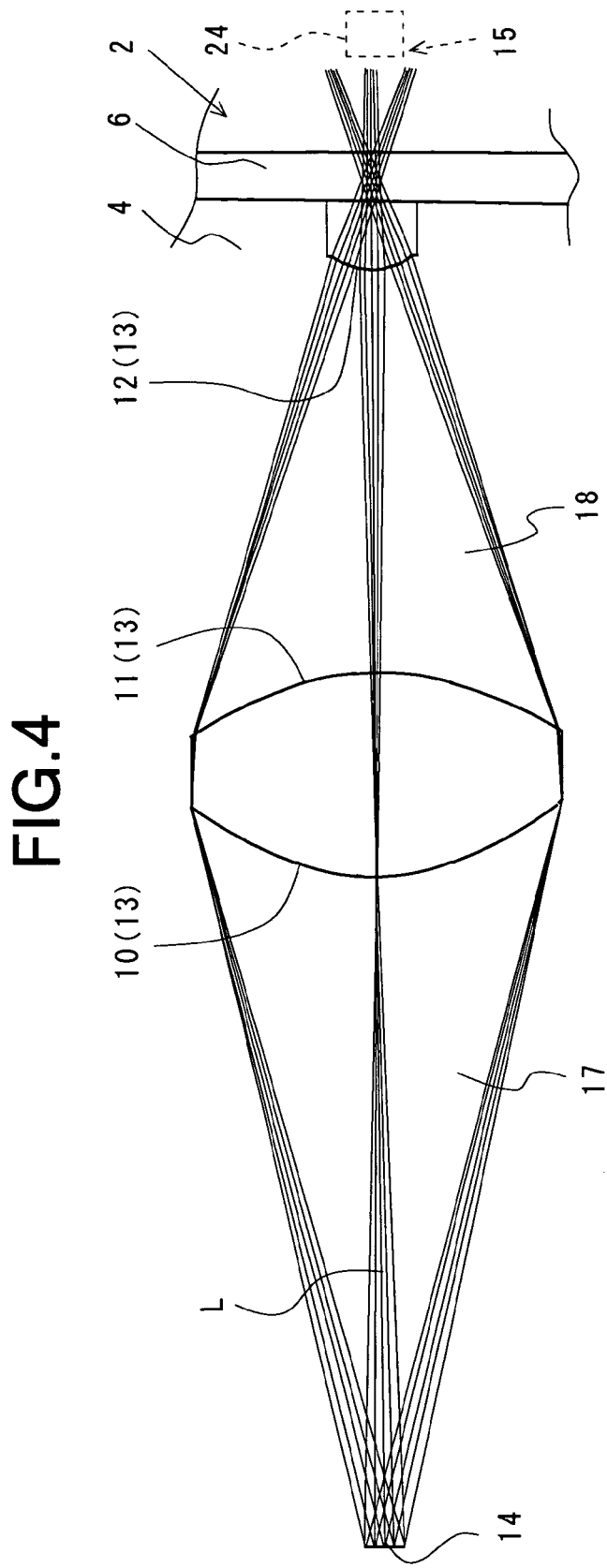
FIG. 4 is an enlarged plan view of a part of the first plate member of the microchip including the optical system in the first preferred embodiment, which shows a condensing state in the optical system.
Figure 6A:
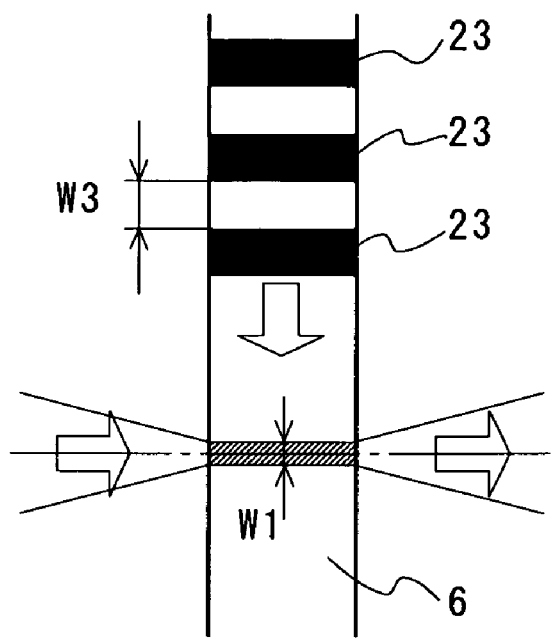
FIG. 6A is a diagram showing a state that bands move before analysis.
Figure 6B:
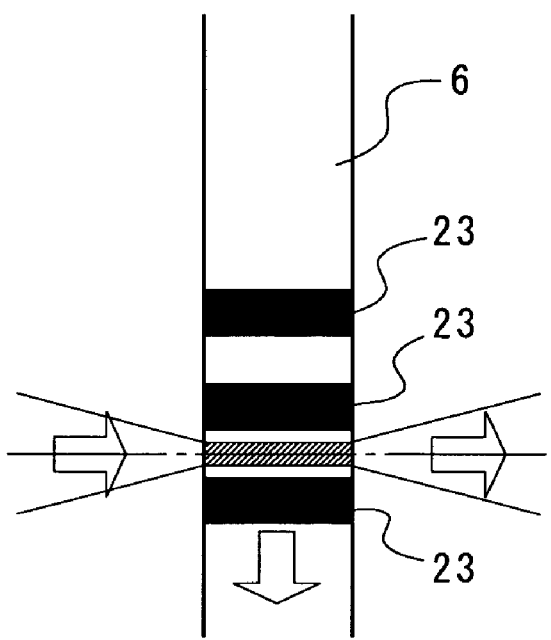
FIG. 6B is a diagram showing a state that bands move during analysis.

As shown in FIG. 4, the above described condensing part 13 comprising the first through third aspherically cylindrical surfaces 10 through 12 in this preferred embodiment is designed so that divergent beams, which leave the outgoing plane of the optical fiber 14 having a core diameter of 50 μm, form an image at the substantially center of the separation passage 6 in width directions thereof and so that the effective light width W1 of light beams, with which a sample in the separation passage 6 is irradiated, is about 25 μm (the power is about 0.5 (=25/50)) On the other hand, in the above described conventional system of Camou et al., with respect to divergent beams leaving the optical fiber 54 having a core diameter of 100 μm, the effective light width of light beams, with which the sample in the separation passage 46 is irradiated, is about 150 μm (the power is about 1.5 (150/100)), so that analysis is carried out by a wider irradiation light width than that in this preferred embodiment. As a result, in the above described conventional system of Camou et al., there are some cases where adjacent bands 23 of the sample in the separation passage 6 may be simultaneously irradiated with light beams. Thus, there are some cases where the detecting means 15 may detect fluorescent emitted from a target sample as well as fluorescence emitted from a sample other than the target sample, so that the precision of detection may deteriorate. However, according to this preferred embodiment, as shown in FIGS. 6A and 6B, the effective light width W1 of light beams, with which the sample in the separation passage 6 is irradiated, is about 25 μm, so that adjacent bands 23 of the sample in the separation passage 6 are not simultaneously irradiated with light beams if the distance W3 between adjacent two of the bands 23 of the sample in the separation passage 6 exceeds the effective light width W1. Throughout the specification, the term "effective light width" means a width of visible light beams observable with the naked eye (the width in directions in which the sample moves due to electrophoresis), in the separation passage 6.

The detecting means 15 comprises a light receiving optical fiber 24 serving as a light receiving element arranged so as to face the third aspherically cylindrical surface 12 via the separation passage 6, and a photoelectric transfer device 25 connected to the light receiving optical fiber 24. The detecting means 15 is designed to output electric signals, which are obtained by photoelectric transfer, to an analyzing device, such as a computer, via an interface (not shown) or the like.

In the microchip 1 to which the optical system 8 with such a construction is applied, the opening portions other than both end portions of each of the first groove 5a forming the sample passage 5 and the second groove 6a forming the separation passage 6, and the opening portions of the first and second spaces 17 and 18 in the analyzing part 9 are closed with the second plate member 3 by fixing the second plate member 3 to the surface 4 of the first plate member 2.

The used state (a state that a sample is separated and identified) of the optical system 8 in this preferred embodiment will be described below. First, in FIG. 1, a sample separating medium is injected into the sample passage 5 and separation passage 6 from through holes 26, which are formed in the second plate member 3 so as to correspond to the end portions of the sample passage 5 and separation passage 6, to be filled in the sample passage 5 and separation passage 6.

Then, as shown in FIG. 1, a sample to be analyzed is injected into one end of the sample passage 5 from one of the through holes 26 of the second plate member 3, and a voltage is applied to both ends of the sample passage 5 to move the sample due to electrophoresis until the front end of the sample passes through the passage crossing portion 7. Then, a voltage is applied to both ends of the separation passage 6 to feed a very small amount of sample, which is positioned at the passage crossing portion 7, into the separation passage 6 to start the separation of the sample. The sample moving in the separation passage 6 due to electrophoresis has different electrophoretic speeds in accordance with in a difference in molecular weight or the like, and is separated into a plurality of bands (a group of materials) 23 until it reaches the analyzing part 9 (see FIGS. 6A and 6B).

As shown in FIG. 4, light beams emitted from the optical fiber 14 sequentially pass through the first through third aspherically cylindrical surfaces 10 through 12 to be condensed, so that the sample (band) reaching the analyzing part 9 is irradiated with the condensed light beams. If the sample is irradiated with the light beams, fluorescent is emitted from the fluorescent label of the sample. The fluorescent emitted from the sample is detected by the detecting means (e.g., light receiving element) 15. On the basis of the results of the detection, the sample is analyzed.

As described above, according to this preferred embodiment, light beams emitted from the optical fiber 14 are condensed, by the first through third aspherically cylindrical surfaces 10 through 12, so as to have a width of about 25 μm, so that the sample in the separation passage 6 is irradiated with the condensed light beams. Therefore, even if the distance between adjacent two of bands 23 is narrower than the distance (150 μm) between adjacent two of bands, which can be precisely measured by the conventional system, the resolution of analysis can be enhanced without simultaneously irradiating adjacent two of bands 23 with light beams. In addition, since the cylindrical surface is formed so as to be aspheric, various aberrations, such as spherical aberration and coma aberration, can be more sufficiently corrected than a cylindrical surface which is formed so as to be spherical.

In addition, according to this preferred embodiment, when bands 23, which move due to electrophoretic at intervals slightly exceeding the irradiation light width (about 25 μm) of light beams with which the sample is irradiated, are analyzed, adjacent two of the bands 23 are not simultaneously irradiated with light beams to emit fluorescent, so that it is possible to precisely analyze the sample (see FIGS. 6A and 6B).

Moreover, according to this preferred embodiment, the power of the condensing part 13 is smaller than that in the above described conventional system of Camou et al. (the power in this preferred embodiment is about 0.5 whereas the power in the conventional system is about 1.5). Therefore, even if the width of each of the bands 23 and the distance between adjacent two of the bands 23 are reduced, it is possible to precisely analyze the sample, so that it is possible to rapidly analyze a smaller amount of sample than the amount of a sample required in the conventional system.

The present invention should not be limited to the above described preferred embodiment wherein the sample moving in the microchannel (separation passage 6) due to electrophoretic is irradiated with light beams, but the invention may be applied to an embodiment wherein a sample in a well is irradiated with light beams.

According to the present invention, the effective light width W1 (25 μm) of light beams, with which the sample is irradiated, can be narrower than the effective light width (150 μm) in the conventional system, and the power can be lower than that in the conventional system. Therefore, light beams emitted from the optical fiber 14 may be condensed by one or two aspherically cylindrical surfaces as long as it is possible to precisely analyze a sample even if the distance between adjacent two of bands 23 is such a distance that it is not precisely measure the sample by the conventional system. In addition, if it is possible to ensure a space for arranging aspherically cylindrical surfaces, light beams emitted from the optical fiber 14 may be condensed by four or more aspherically cylindrical surfaces.

In the above described preferred embodiment, a light reflecting means may be formed on a surface which faces the condensing part 13 of the second plate member 3, and light reflecting means (not shown) may be formed on both sides and bottom faces 20 and 21 of the first and second spaces 17 and 18 of the first plate member 2. Thus, it is possible to prevent light beams from leaking out, so that it is possible to effectively utilize the light beams as illuminating light.

In the above described preferred embodiment, an aspheric surface obtained by rotating the curve of FIG. 7 about Z-axis may be used in place of the first through third aspherically cylindrical surfaces 10 through 12.

In the above describe preferred embodiment, the optical system uses aspherically cylindrical surfaces for three lens surfaces forming the condensing part 13. However, the present invention should not be limited thereto, but the condensing part 13 may be formed by, e.g., aspherically toroidal surfaces, in place of the cylindrical surfaces. If the toroidal surfaces are used, it is possible to condense light beams on a plane perpendicular to the surface 4 of the first plate member 2. Furthermore, after the microchip is formed of polydimethyl siloxane (PDMS) or the like, if a material having predetermined elasticity is used, an optical system for a micro analyzing system having a toroidal surface can be produced by a molding die.

Second Preferred Embodiment

Figure 8:
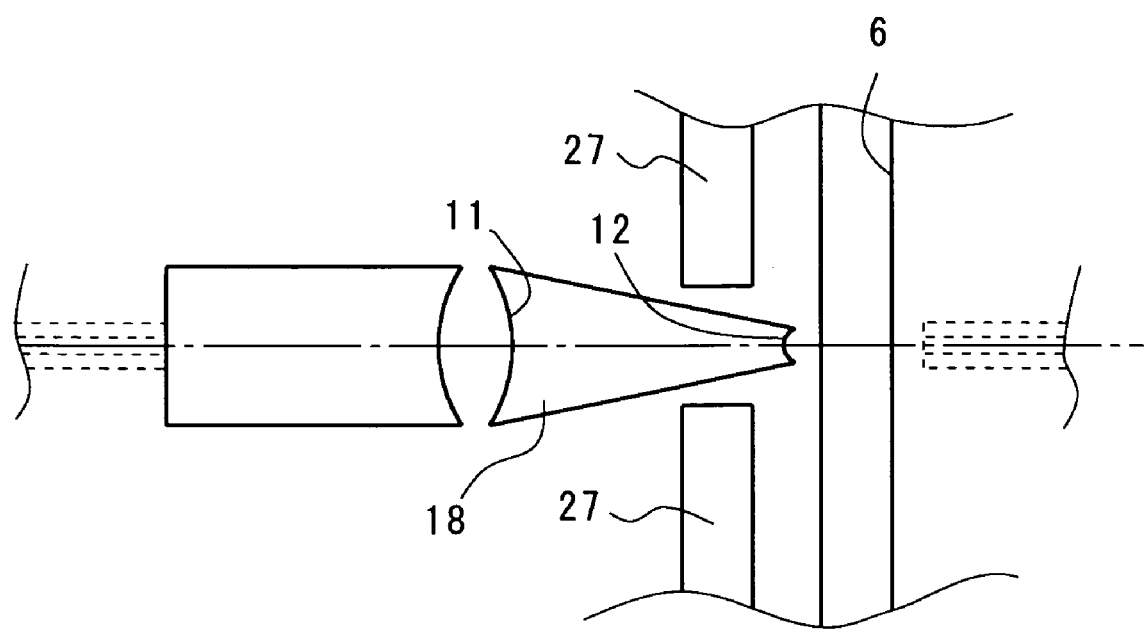
FIG. 8 is an enlarged plan view of a part of a first plate member of a microchip including the second preferred embodiment of an optical system for a micro analyzing system according to the present invention.
Figure 9:
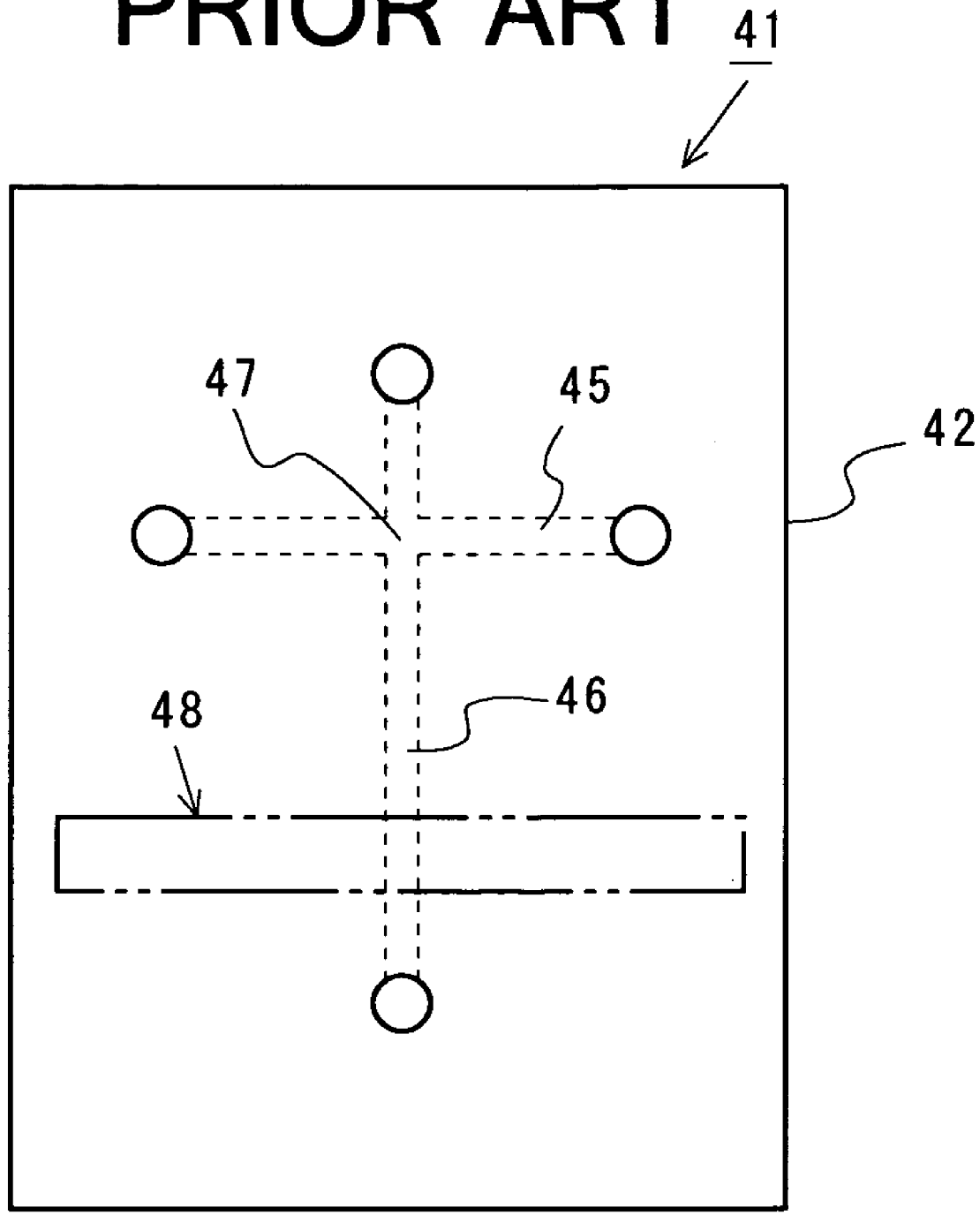
FIG. 9 is a plan view of a microchip including a conventional optical system for a micro analyzing system.
Figure 10:
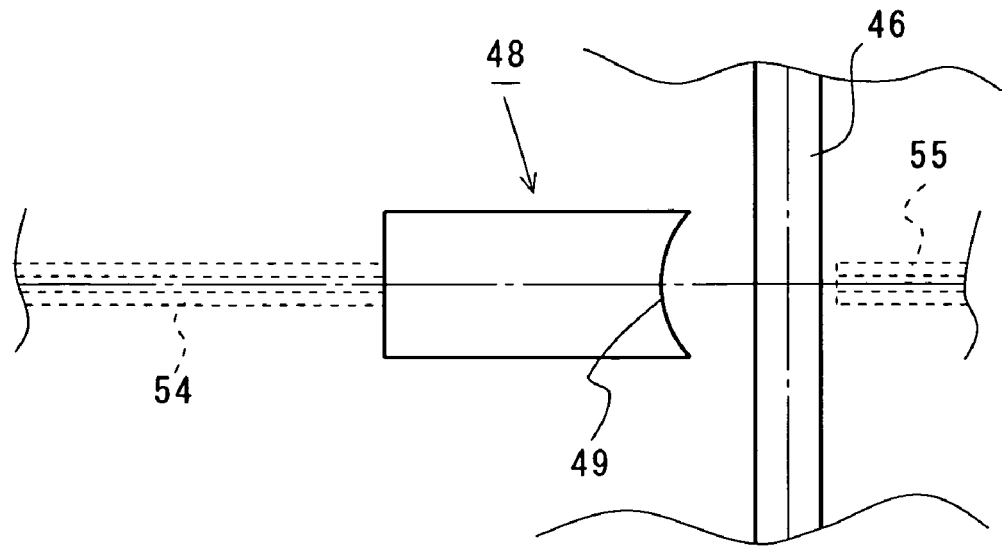
FIG. 10 is an enlarged plan view of the conventional optical system.
Figure 11:
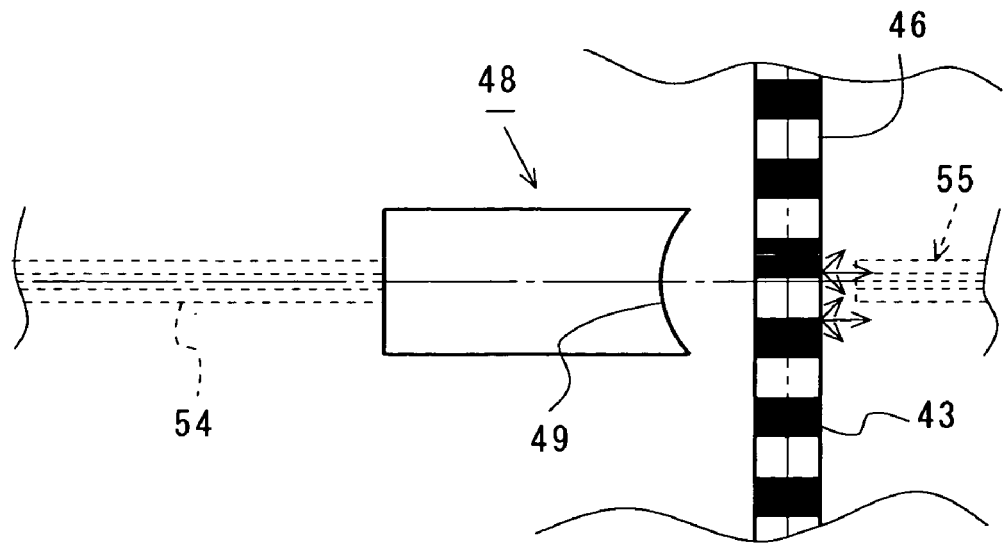
FIG. 11 is an enlarged plan view showing the operating state of the conventional optical system.

FIG. 8 is a plan view of a part of a first plate member of a microchip, to which the second preferred embodiment of an optical system for a micro analyzing system according to the present invention is applied.

As shown in FIG. 8, stray light shielding grooves 27 and 27, which extend substantially in parallel to the separation passage 6 and which substantially have the same cross section as that of the separation passage 6, are formed between the second aspherically cylindrical surface 11 and the third aspherically cylindrical surface 12 so that one end of each of the stray light shielding grooves 27 and 27 is positioned in the vicinity of the second space 18.

With such a construction, stray light leaking out in the vicinity of the condensing part 13 of the first plate member 2 is totally reflected on the sides of the stray light shielding grooves 27 and 27 to prevent stray light from entering the separation passage 6, so that it is possible to prevent the precision of analysis from being deteriorated by stray light.

As described above, according to the present invention, the condensing part using the aspherically cylindrical surfaces condenses light beams at a lower power than that in the conventional system (so as to reduce the effective light width) to irradiate only a target sample, which is arranged in a recessed portion to be analyzed, with the condensed narrow light beams, so that it is possible to precisely and rapidly analyze the target sample.

While the present invention has been disclosed in terms of the preferred embodiment in order to facilitate better understanding thereof, it should be appreciated that the invention can be embodied in various ways without departing from the principle of the invention. Therefore, the invention should be understood to include all possible embodiments and modification to the shown embodiments which can be embodied without departing from the principle of the invention as set forth in the appended claims.

What is claimed is:

1. An optical system for an analyzing system for irradiating a sample with light beams to optically analyze the sample, said optical system comprising:

a plate member having a first space, a second space, and a third space for receiving the sample therein;

a first lens surface, formed on one end face of said first space, for receiving light beams from a light source via a light guide passage, said first lens surface being an aspheric surface which is convex toward said light guide passage;

a second lens surface, formed on one end face of said second space, for receiving the light beams passing through said first lens surface, said second lens surface being an aspheric surface which is concave toward said first lens surface; and a third lens surface, formed on the other end face of said second space, for receiving the light beams passing through said second lens surface, said third lens surface being an aspheric surface which is convex toward said second lens surface, said first, second and third lens surfaces being associated with each other for condensing the light beams toward said third space.

2. An optical system as set forth in claim 1, wherein each of said aspheric surfaces is an aspherically cylindrical surface.

3. An optical system as set forth in claim 1, wherein said third space is a channel for allowing said sample to move due to electrophoresis.

4. An optical system as set forth in claim 1, wherein said light guide passage is an optical fiber.

5. An optical system as set forth in claim 1, wherein said first space is formed in said plate member between said light source and said second space so as to substantially have the same width between the other end face thereof, which faces said light guide passage, and said one end face thereof serving as said first lens surface, and said second space is formed in said plate member between said first space and said third space so as to have a width gradually decreasing toward said third lens surface as a distance from said second lens surface increases.

6. An optical system for an analyzing system for irradiating a sample with light beams to optically analyze the sample, said optical system comprising:

a plate member;

a first space formed in said plate member, said first space having a first lens surface on one end face thereof for receiving light beams from a light source via a light guide passage, said first lens surface being an aspheric surface which is convex toward said light guide passage;

a second space formed in said plate member, said second space having a second lens surface on one end face thereof for receiving the light beams passing through said first lens surface, said second lens surface being an aspheric surface which is concave toward said first lens surface, said second space having a third lens surface on the other end face thereof for receiving the light beams passing through said second lens surface, said third lens surface being an aspheric surface which is convex toward said second lens surface; and a third space, formed in said plate member, for receiving the sample therein, said first, second and third lens surfaces being associated with each other for condensing the light beams toward said third space.

7. An optical system as set forth in claim 6, wherein each of said aspheric surfaces is an aspherically cylindrical surface.

8. An optical system as set forth in claim 6, wherein said third space is a channel for allowing said sample to move due to electrophoresis.

9. An optical system as set forth in claim 6, wherein said light guide passage is an optical fiber.

10. An optical system as set forth in claim 6, wherein said first space is formed between said light source and said second space so as to substantially have the same width between the other end face thereof, which faces said light guide passage, and said one end face thereof serving as said first lens surface, and said second space is formed between said first space and said third space so as to have a width gradually decreasing toward said third lens surface as a distance from said second lens surface increases.

* * * * *